（12）United States Patent
Fortin et al.

(10) Patent No.: US 11,490,904 B2
(45) Date of Patent: Nov. 8, 2022

(54) ORTHOPAEDIC SURGICAL INSTRUMENT ASSEMBLY FOR REAMING A PATIENT'S ACETABULUM

(71) Applicant: DePuy Ireland Unlimited Company, Ringaskiddy (IE)

(72) Inventors: Michael Fortin, Acushnet, MA (US); John Cuneo, Norton, MA (US); Rod Cameron, Franklin, MA (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 235 days.

(21) Appl. No.: 16/774,109

(22) Filed: Jan. 28, 2020

(65) Prior Publication Data

US 2020/0155172 A1    May 21, 2020

Related U.S. Application Data

(62) Division of application No. 14/503,289, filed on Sep. 30, 2014, now Pat. No. 10,543,003.

(51) Int. Cl.
*A61B 17/16* (2006.01)
*C23F 1/02* (2006.01)
(Continued)

(52) U.S. Cl.
CPC ...... *A61B 17/1666* (2013.01); *A61B 17/1615* (2013.01); *C23F 1/02* (2013.01); *C23F 1/14* (2013.01); *A61B 2017/00526* (2013.01)

(58) Field of Classification Search
CPC ............ A61B 17/1666; A61B 17/1668; A61B 17/1664; A61B 17/1659
(Continued)

(56) References Cited

U.S. PATENT DOCUMENTS 3,045,321 A * 7/1962 Mcdermott ............ B23D 73/00
407/29.1
4,023,572 A   5/1977 Weigand et al.
(Continued)

FOREIGN PATENT DOCUMENTS

DE            2437772 A1    2/1976
DE    202010005376 U1    8/2010
(Continued)

OTHER PUBLICATIONS

International Search Report and Written Opinion, International Application No. PCT/GB2014/053706, dated Apr. 14, 2015, 12 pages.
(Continued)

*Primary Examiner* — Matthew J Lawson
(74) *Attorney, Agent, or Firm* — Barnes & Thornburg LLP

(57) ABSTRACT

An orthopaedic surgical instrument assembly includes a hemispherical component having a convex outer surface extending from a circular rim to an apex point, and a plurality of cutting teeth extending outwardly from the outer surface between the circular rim and the apex point. Each cutting tooth of the plurality of cutting teeth includes an elongated cutting edge that is positioned on an arced imaginary line of a plurality of arced imaginary lines extending outwardly from the apex point of the hemispherical component. A method of manufacturing an orthopaedic surgical instrument assembly is also disclosed.

9 Claims, 11 Drawing Sheets

(51) Int. Cl.
*C23F 1/14* (2006.01)
*A61B 17/00* (2006.01)

(58) Field of Classification Search
USPC .................................................. 606/80–81
See application file for complete search history.

(56) References Cited

U.S. PATENT DOCUMENTS

| | | | |
|---|---|---|---|
| 4,662,891 | A | 5/1987 | Noiles |
| 4,712,951 | A | 12/1987 | Brown |
| 4,802,468 | A | 2/1989 | Powlan |
| 5,116,165 | A | 5/1992 | Salyer |
| 5,295,992 | A | 3/1994 | Cameron |
| 5,302,234 | A * | 4/1994 | Grace ................ A61B 17/1666 216/47 |
| 5,431,657 | A | 7/1995 | Rohr |
| 5,462,548 | A | 10/1995 | Pappas et al. |
| 5,540,697 | A | 7/1996 | Rehmann et al. |
| 5,584,837 | A | 12/1996 | Petersen |
| 5,817,096 | A | 10/1998 | Salyer |
| 5,879,355 | A | 3/1999 | Ullmark |
| 5,976,148 | A | 11/1999 | Charpenet et al. |
| 6,015,411 | A | 1/2000 | Ohkoshi et al. |
| 6,102,915 | A | 8/2000 | Bresler et al. |
| 6,168,600 | B1 | 1/2001 | Grace et al. |
| 6,221,076 | B1 | 4/2001 | Mbrektsson et al. |
| 6,409,732 | B1 | 6/2002 | Salyer |
| 6,730,094 | B2 | 5/2004 | Salyer et al. |
| 6,875,217 | B2 | 4/2005 | Wolford |
| 7,118,575 | B2 | 10/2006 | Wolford |
| 7,220,264 | B1 | 5/2007 | Hershberger |
| 7,335,207 | B1 | 2/2008 | Smith |
| 7,621,921 | B2 | 11/2009 | Parker |
| 7,744,602 | B2 | 6/2010 | Teeny et al. |
| 7,763,031 | B2 | 7/2010 | Tulkis |
| 8,123,815 | B2 | 2/2012 | Meridew et al. |
| 8,308,810 | B2 | 11/2012 | Meridew |
| 8,357,163 | B2 | 1/2013 | Sidebotham et al. |
| 8,435,243 | B2 | 5/2013 | White et al. |
| 8,556,897 | B2 | 10/2013 | Sidebotham et al. |
| 8,679,124 | B2 | 3/2014 | Lechot et al. |
| 8,771,275 | B2 | 7/2014 | Xie et al. |
| 8,870,886 | B2 | 10/2014 | Burgi |
| 9,375,221 | B2 * | 6/2016 | Edwards .............. A61B 17/157 |
| 9,439,781 | B2 | 9/2016 | Gibson |
| 10,543,003 | B2 | 1/2020 | Fortin et al. |
| 2003/0050645 | A1 | 3/2003 | Parker et al. |
| 2003/0130741 | A1 | 7/2003 | McMinn |
| 2004/0073224 | A1 | 4/2004 | Bauer |
| 2004/0073226 | A1 | 4/2004 | Cotting et al. |
| 2004/0117029 | A1 | 6/2004 | Lewis et al. |
| 2004/0133210 | A1 | 7/2004 | Wolford |
| 2004/0143271 | A1 | 7/2004 | Wolford |
| 2005/0038443 | A1 | 2/2005 | Hedley et al. |
| 2005/0085823 | A1 | 4/2005 | Murphy |
| 2005/0085915 | A1 * | 4/2005 | Steinberg ............. A61F 2/3609 623/17.16 |
| 2005/0228394 | A1 | 10/2005 | Bihary et al. |
| 2005/0261694 | A1 | 11/2005 | Orton et al. |
| 2006/0025774 | A1 | 2/2006 | Fishbein et al. |
| 2006/0079906 | A1 | 4/2006 | Timperley et al. |
| 2006/0089633 | A1 * | 4/2006 | L. Bleich ......... A61B 17/32002 606/32 |
| 2006/0217730 | A1 | 9/2006 | Termanini |
| 2007/0198022 | A1 * | 8/2007 | Lang .................... A61B 17/157 606/88 |
| 2007/0203583 | A1 | 8/2007 | Slone |
| 2007/0233132 | A1 | 10/2007 | Valia |
| 2007/0276394 | A1 | 11/2007 | Johnson et al. |
| 2008/0009952 | A1 | 1/2008 | Hodge |
| 2008/0195106 | A1 | 8/2008 | Sidebotham et al. |
| 2008/0215159 | A1 | 9/2008 | Stamp |
| 2009/0088757 | A1 | 4/2009 | Tulkis |
| 2009/0163921 | A1 | 6/2009 | Lechot et al. |
| 2010/0069908 | A1 | 3/2010 | Sidebotham et al. |
| 2010/0145342 | A1 * | 6/2010 | Grace ................ A61B 17/1666 606/81 |
| 2010/0168749 | A1 | 7/2010 | Sidebotham et al. |
| 2010/0168752 | A1 | 7/2010 | Edwards |
| 2010/0186477 | A1 | 7/2010 | Barthelemy et al. |
| 2010/0272533 | A1 | 10/2010 | Hecht |
| 2011/0202060 | A1 | 8/2011 | White et al. |
| 2011/0208202 | A1 | 8/2011 | Zumsteg et al. |
| 2011/0213372 | A1 | 9/2011 | Keefer et al. |
| 2012/0185059 | A1 | 7/2012 | Vankoski et al. |
| 2012/0191099 | A1 * | 7/2012 | Victor ................ A61B 17/1666 606/81 |
| 2013/0131741 | A1 | 5/2013 | Kourtis et al. |
| 2013/0211407 | A1 | 8/2013 | Geebelen |
| 2013/0245628 | A1 * | 9/2013 | Sidebotham ........... A61B 17/16 606/80 |
| 2013/0267957 | A1 | 10/2013 | Stamp |
| 2013/0325139 | A1 | 12/2013 | Steiner et al. |
| 2014/0114321 | A1 | 4/2014 | Davenport et al. |
| 2014/0163564 | A1 | 6/2014 | Bollinger |
| 2014/0228854 | A1 | 8/2014 | Witt et al. |
| 2014/0276852 | A1 * | 9/2014 | Young ................ A61B 17/1668 606/85 |
| 2014/0324183 | A1 | 10/2014 | Springer et al. |
| 2015/0100060 | A1 | 4/2015 | Black |
| 2015/0366568 | A1 | 12/2015 | Victor et al. |
| 2016/0089156 | A1 | 3/2016 | Fortin et al. |
| 2016/0089158 | A1 | 3/2016 | Fortin et al. |
| 2016/0175112 | A1 | 6/2016 | Pruvost et al. |
| 2017/0000502 | A1 * | 1/2017 | Mroczkowski .... A61B 17/1666 |
| 2017/0014141 | A1 | 1/2017 | Cameron et al. |

FOREIGN PATENT DOCUMENTS

| | | |
|---|---|---|
| DE | 102011000976 A1 | 8/2012 |
| EP | 147339 A2 | 7/1985 |
| EP | 1183998 A2 | 3/2002 |
| JP | 2006288863 A | 10/2006 |
| RU | 1804314 A3 | 3/1993 |
| SU | 1568985 A1 | 6/1990 |
| WO | 2007121313 A2 | 10/2007 |
| WO | 2015092377 A1 | 6/2015 |

OTHER PUBLICATIONS

International Search Report and Written Opinion, International Application No. PCT/US2015/051634, dated Mar. 2, 2016, 15 pages.

International Search Report and Written Opinion for Application No. PCT/US2015/051666, dated Mar. 8, 2016, 9 pages.

* cited by examiner

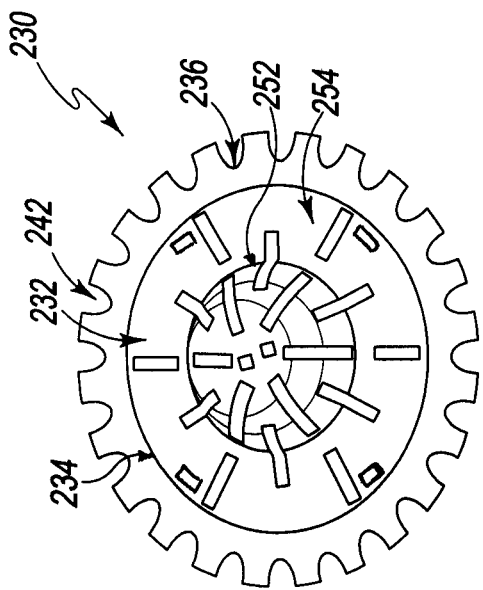
Fig. 15
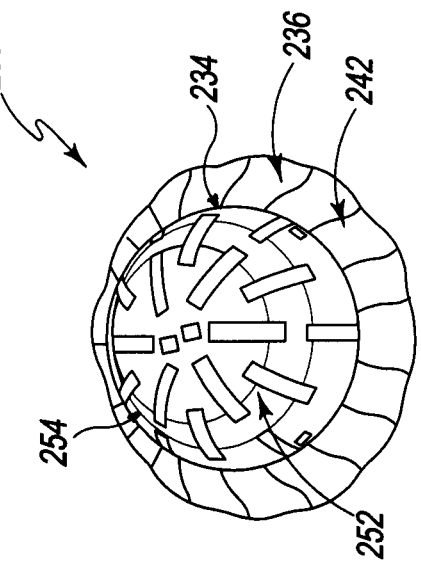
Fig. 16
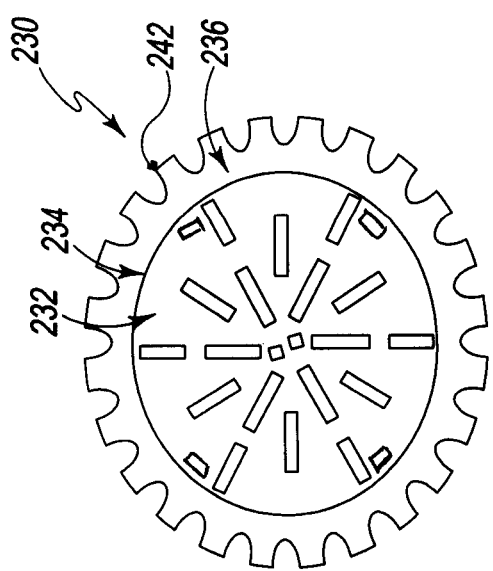
Fig. 17
Fig. 18

ORTHOPAEDIC SURGICAL INSTRUMENT ASSEMBLY FOR REAMING A PATIENT'S ACETABULUM

This application is a divisional application and claims priority to U.S. patent application Ser. No. 14/503,289, now U.S. Pat. No. 10,543,003, the entirety of which is expressly incorporated herein by reference.

CROSS-REFERENCE

Cross-reference is made to U.S. utility patent application "ORTHOPAEDIC SURGICAL INSTRUMENT ASSEMBLY FOR REAMING A PATIENT'S ACETABULUM," U.S. patent application Ser. No. 14/503,293, now U.S. Pat. No. 10,092,304, the entirety of which is expressly incorporated herein by reference.

TECHNICAL FIELD

The present disclosure relates generally to orthopaedic surgical instruments and more particularly to orthopaedic surgical instruments used for joint arthroplasty.

BACKGROUND

Joint arthroplasty is a well-known surgical procedure by which a diseased and/or damaged natural joint is replaced by a prosthetic joint. For example, in a hip arthroplasty surgical procedure, a prosthetic hip replaces a patient's natural hip. A typical prosthetic hip includes an acetabular orthopaedic prosthesis and/or femoral head orthopaedic prosthesis. A typical acetabular orthopaedic prosthesis includes an acetabular cup, which is secured to the patient's natural acetabulum, and an associated polymer bearing or ring.

To facilitate the replacement of the natural joint with an acetabular orthopaedic prosthesis, orthopaedic surgeons may use a variety of orthopaedic surgical instruments such as, for example, reamers, drill guides, drills, and/or other surgical instruments. Typically, such orthopaedic surgical instruments are generic with respect to the patient such that the same orthopaedic surgical instrument may be used on a number of different patients during similar orthopaedic surgical procedures.

SUMMARY

According to one aspect of the present disclosure, an orthopaedic surgical instrument assembly includes a hemispherical component having a convex outer surface extending from a circular rim to an apex point, and a plurality of cutting teeth extending outwardly from the outer surface between the circular rim and the apex point. Each cutting tooth of the plurality of cutting teeth includes an elongated cutting edge that is positioned on an arced imaginary line of a plurality of arced imaginary lines extending outwardly from the apex point of the hemispherical component.

In some embodiments, the circular rim may define a first imaginary plane. A second imaginary plane may extend orthogonal to the first imaginary plane through the apex point, and a first arced imaginary line of the plurality of arced imaginary lines may lie in the second imaginary plane. At least two cutting teeth of the plurality of cutting teeth may be positioned on the first arced imaginary line. The at least two cutting teeth may include a first pair of cutting teeth positioned on the first arced imaginary line on a first side of the hemispherical component, and a second pair of cutting teeth positioned on the first arced imaginary line on a second side of the hemispherical component opposite the first side. In some embodiments, a third imaginary plane may extend orthogonal to the first imaginary plane through the apex point, and a second arced imaginary line of the plurality of arced imaginary lines may lie in the third imaginary plane. At least one cutting tooth of the plurality of cutting teeth may be positioned on the second arced imaginary line. The at least two cutting teeth of the plurality of cutting teeth may include a first cutting tooth spaced apart from a second cutting tooth on the first imaginary line such that a gap is defined between the first cutting tooth and the second cutting tooth. The at least one cutting tooth on the second arced imaginary line may be aligned with the gap defined between the first cutting tooth and the second cutting tooth.

In some embodiments, each cutting tooth of the plurality of cutting teeth may include a first sidewall extending outwardly from the outer surface, a second sidewall extending outwardly from the outer surface, and an outer wall connecting the first sidewall and the second sidewall. In some embodiments, each cutting tooth of the plurality of cutting teeth may be positioned above an oblong slot. The oblong slot may have a longitudinal axis extending parallel to the arced imaginary line.

In some embodiments, the hemispherical component may further include a cutting tooth positioned adjacent to the apex point of the hemispherical component. In some embodiments, the hemispherical component may be formed from a metallic material.

According to another aspect of the present disclosure, an orthopaedic surgical instrument includes a hemispherical component having a convex outer surface extending from a circular rim to an apex point, and a plurality of cutting teeth extending outwardly from the outer surface between the circular rim and the apex point. The circular rim defines a base imaginary plane, and each cutting tooth of the plurality of cutting teeth is positioned on one of a plurality of tooth imaginary planes. Each tooth imaginary plane extends orthogonal to the base imaginary plane and through the apex point.

In some embodiments, each cutting tooth of the plurality of cutting teeth may be positioned above an oblong slot. The oblong slot may have a longitudinal axis extending parallel to one of the tooth imaginary planes. In some embodiments, the hemispherical component may be formed from a metallic material.

In some embodiments, the plurality of cutting teeth may include a pair of cutting teeth positioned on a first imaginary plane, and a cutting tooth positioned on a second imaginary plane. The cutting tooth may be aligned with a gap defined between the pair of cutting teeth. The pair of cutting teeth positioned on the first imaginary plane may be the only cutting teeth extending outwardly from the outer surface between the apex point and a first point on the circular rim on the first imaginary plane. The cutting tooth positioned on the second imaginary plane may be the only cutting tooth extending outwardly from the outer surface between the apex point and a second point on the circular rim on the second imaginary plane. In some embodiments, the hemispherical component may further include a cutting tooth positioned adjacent to the apex point of the hemispherical component.

According to yet another aspect of the present disclosure, a method of manufacturing an orthopaedic surgical instrument includes chemically-etching a sheet to form a plurality of blanks including a plurality of stenciled shapes, forming a hemispherical shell from the blank, the hemispherical shell including a convex outer surface and a plurality of flanges extending outwardly from the convex outer surface, each flange including at least one of the plurality of stenciled shapes, and applying a chemical etch to the stenciled shapes to form a cutting tooth and a cutting edge in each one of the flanges.

In some embodiments, each blank of the plurality of blanks may include a circular body and a flange coupled to the circular body. The flange may have a plurality of notches formed therein. The method may further comprise removing the flange from the circular body. In some embodiments, forming the hemispherical shell from the blank may include hydroforming the hemispherical shell from the blank.

In some embodiments, chemically-etching the hemispherical shell may include forming a plurality of slots beneath the cutting edges of the cutting teeth. In some embodiments, the method may include applying a photoresist film to the sheet.

According to another aspect of the present disclosure, a surgical instrument assembly includes a metallic hemispherical component and a driver component removably coupled to the hemispherical component. The metallic hemispherical component has a convex outer surface configured to engage a patient's natural acetabulum, a concave inner surface positioned opposite the outer surface and defining a cavity in the hemispherical component, a plurality of cutting teeth extending outwardly from the outer surface, and a plurality of apertures defined in the inner surface. The driver component has a shank and a plurality of ribs secured to, and extending outwardly from, the shank. Each rib has a tab that is received in a corresponding aperture of the hemispherical component to secure the driver component to the hemispherical component.

In some embodiments, the cavity may be hemispherical. In some embodiments, each aperture of the plurality of apertures may extend through the inner surface and the outer surface. Each aperture may be rectangular-shaped.

In some embodiments, the driver component may be formed from a polymeric material. The polymeric material may be injection-molded plastic.

In some embodiments, each rib of the plurality of ribs may include a strut extending outwardly from the shank, an arm defining an outer end of the rib, and a tab extending from the arm and being received in the corresponding aperture of the hemispherical component. Each arm of each rib may include an arcuate outer surface that engages the concave inner surface of the hemispherical component. In some embodiments, the struts may be arranged to receive a surgical instrument to transmit rotational power from the surgical instrument to the hemispherical component. Additionally, in some embodiments, the driver component may be formed as a single monolithic component. In some embodiments still, the inner surface may extend inwardly from a circular rim of the hemispherical component to define the cavity, and the hemispherical component may include a plurality of retainers that extend from the circular rim to engage the plurality of ribs of the driver component. Each arm may include a shoulder that is positioned between a corresponding pair of retainers of the plurality of retainers of the hemispherical component.

In some embodiments, an angle may be defined between each rib of the plurality of ribs. Each angle may have a magnitude of approximately ninety degrees.

According to another aspect of the present disclosure, a surgical instrument assembly includes a first component, a second component, and a surgical instrument. The first component has an outer surface configured to engage a patient's natural acetabulum, an inner surface positioned opposite the outer surface and defining a hemispherical cavity in the first component, a plurality of cutting teeth extending outwardly from the outer surface, and a plurality of apertures defined in the inner surface. The second component has a monolithic frame, and the frame has a plurality of tabs. Each tab is received in a corresponding aperture of the plurality of apertures. The surgical instrument is configured to be secured to the frame of the second component to transmit rotational power from the surgical instrument to the first component.

In some embodiments, the first component may be formed from a metallic material. The second component may be formed from a polymeric material.

In some embodiments, the frame of the second component may include a shank, a strut extending outwardly from the shank, and an arm defining an outer end of the rib. Each strut may be secured to the surgical instrument, and each arm may have a tab of the plurality of tabs extending outwardly therefrom.

In some embodiments, the inner surface may extend inwardly from a circular rim of the first component to define the hemispherical cavity. The first component may include a plurality of retainers that extend from the circular rim to engage the frame of the second component.

According to yet another aspect of the present disclosure, an acetabular reaming head assembly includes a metallic component and a polymeric driver component removably coupled to the metallic component. The metallic component includes a plurality of cutting teeth configured to engage a patient's natural acetabulum. The driver component includes a shank configured to receive a surgical instrument to transmit rotational power from the surgical instrument to the metallic component. The metallic component includes a plurality of tabs, and each tab is received in a corresponding aperture defined in the driver component.

In some embodiments, the driver component may include a circular rim and an inner wall that extends inwardly from the circular rim to define a cavity in the driver component. The metallic component may extend outwardly from the cavity defined in the driver component.

BRIEF DESCRIPTION OF THE DRAWINGS

The detailed description particularly refers to the following figures, in which:

FIG. 15 is a plan view of the metallic blank of FIG. 12 prior to the press operation of the method of FIG. 10;

FIGS. 16-18 are perspective views of the metallic blank of FIG. 12 during the press operation of the method of FIG. 10;

DETAILED DESCRIPTION OF THE DRAWINGS

Figure 1:
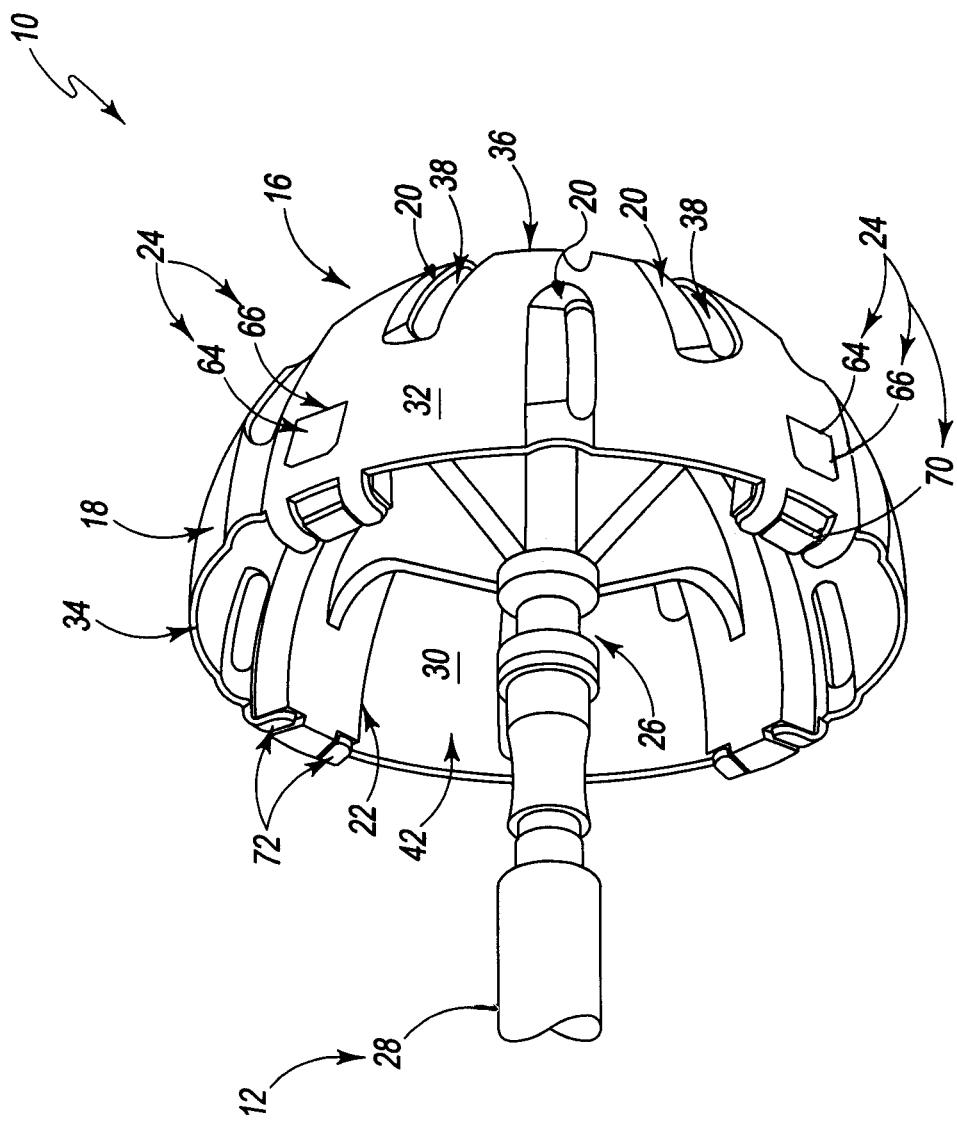
FIG. 1 is a perspective view of one embodiment of an acetabular surgical instrument assembly for use with a rotary power tool.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, one embodiment of an orthopaedic surgical instrument assembly 10 is illustrated. The orthopaedic surgical instrument assembly 10 is adapted for use with a rotary power tool 12 to resect a portion of a patient's bone. In the illustrative embodiment, the orthopaedic surgical instrument assembly 10 includes a reamer 16 that is configured to resect a patient's natural acetabulum. In other embodiments, the reamer 16 may be configured for use with other portions of the patient's body, such as, for example, the distal humerus, proximal tibia, distal femur, and so forth.

As shown in FIG. 1, the reamer 16 includes a hemispherical component 18 and a plurality of cutting teeth 20 that are formed on the component 18. The reamer 16 is illustratively formed as a single, monolithic metallic component, but it should be appreciated that in other embodiments the reamer 16 may be formed as a composite material. In the illustrative embodiment, the reamer 16 is formed, for example, from titanium or stainless steel. In other embodiments, part of the reamer 16 may be formed from a polymeric material such as, for example, plastic, while the cutting surfaces are coated with a metallic material. For example, the hemispherical component 18 may be formed from a polymeric material, while the cutting teeth 20 may be coated or formed with a metallic cutting edge.

The reamer 16 is secured to a reamer driver 22 via a plurality of locking features 24. As described in greater detail below, the locking features 24 permit the reamer 16 to be fixed to the driver 22 during a surgical procedure and detached from the driver 22 following the surgical procedure. In the illustrative embodiment, the reamer 16 is configured to be reused in multiple surgical procedures, and the driver 22 is configured to be disposed following a single use. As shown in FIG. 1, the driver 22 is configured to be removably coupled to the rotary power tool 12.

In the illustrative embodiment, the reamer driver 22 includes a shank 26 that is configured to be engaged with an output shaft 28 of the rotary power tool 12. When the tool 12 is attached, rotary power generated by the rotary power tool 12 is transmitted to the reamer 16 via the reamer driver 22. In that way, the driver 22 acts as the driver component for the assembly 10.

The driver 22 is illustratively formed as a single, monolithic polymer component, but it should be appreciated that in other embodiments the driver 22 may be formed as a composite material. In the illustrative embodiment, the driver 22 is formed from plastic such as, for example, injection-molded plastic. In other embodiments, part of the driver 22 may be formed from plastic while other parts of the driver may be formed from metal. In still other embodiments, the driver 22 may be formed exclusively from a metallic material. It should be appreciated that the driver 22 may also be configured for reuse in multiple surgical procedures.

Figure 2:
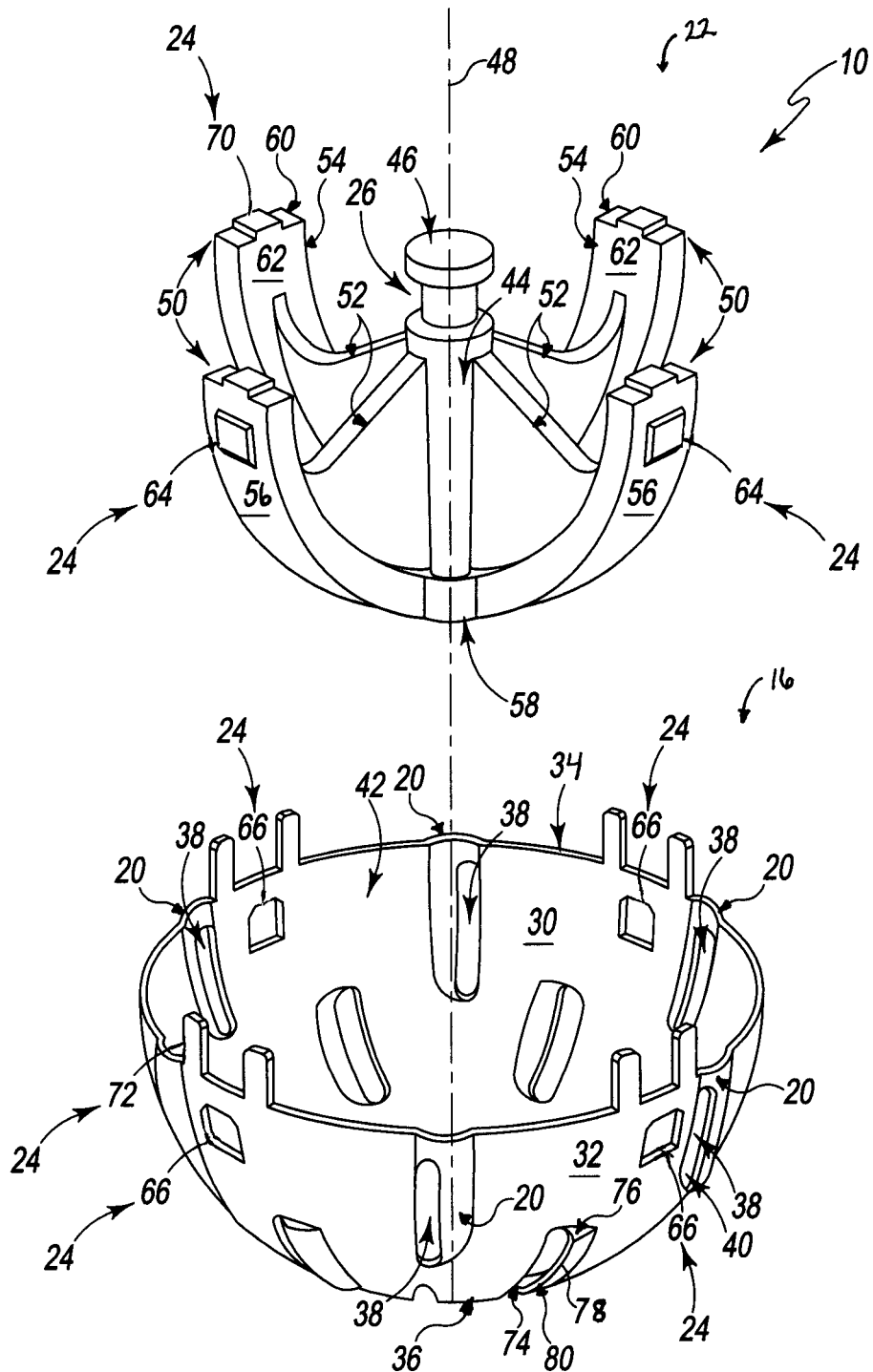
FIG. 2 is an exploded perspective view of the acetabular surgical instrument assembly of FIG. 1.

Referring now to FIG. 2, the hemispherical component 18 of the reamer 16 includes a concave inner surface 30 that is arranged opposite a convex outer surface 32. A substantially planar rim 34 extends between the surfaces 30, 32. The convex outer surface 32 extends from the rim surface 34 to an apex point 36 of the component 18. When the orthopaedic surgical instrument assembly 10 is used during the hip arthroplasty procedure, the apex point 36 represents the medial-most point of the reamer 16.

The cutting teeth 20 of the reamer 16 are arranged on the convex outer surface 32 of the hemispherical component 18. In the illustrative embodiment, each tooth 20 extends longitudinally away from the rim surface 34 toward the apex point 36 and has an oblong shape. Each tooth 20 is also positioned above an oblong slot 38 defined in the surface 32. As shown in FIG. 2, the slot 38 extends through the surfaces 30, 32 and opens into a cavity 42 defined in the component 18. A passageway 40 is defined between each tooth 20 and corresponding slot 38, and each passageway 40 is sized to permit resected bone to pass into the cavity 42, as described in greater detail below.

As shown in FIG. 2, the concave surface 30 of the hemispherical component 18 extends longitudinally inwardly from the rim surface 34 to define the cavity 42 in the component 18. The cavity 42 is sized to receive the driver 22 when the orthopaedic surgical instrument assembly 10 is assembled. While the cavity 42 is illustratively shown as hemispherical, it should be appreciated that in other embodiments the cavity 42 may take other geometric forms.

The driver 22 includes a central core 44, and the shank 26 extends outwardly from the core 44 to a tip 46 configured to be engaged with the output shaft 28 of the rotary power tool 12. As shown in FIG. 2, the central core 44 and the shank 26 cooperate to define a rotational axis 48 that extends through the apex point 36 of the hemispherical component 18 when the component 18 is secured to the driver 22. The driver 22 includes a plurality of ribs 50 that extend outwardly from the core 44. In the illustrative embodiment, the driver 22 includes four ribs 50 that are positioned approximately ninety degrees apart. In other embodiments, the driver 22 may include additional or fewer ribs 50 spaced apart from one another by angles other than ninety degrees.

Figure 6:
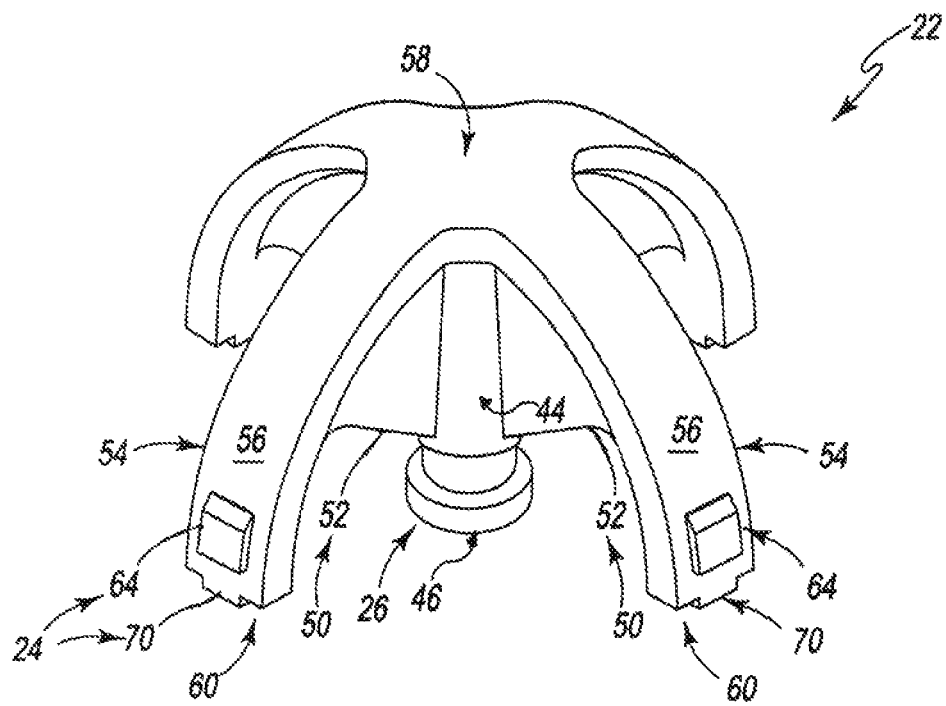
FIG. 6 is a perspective view of a driver component of the acetabular surgical instrument assembly of FIG. 1.
Figure 7:
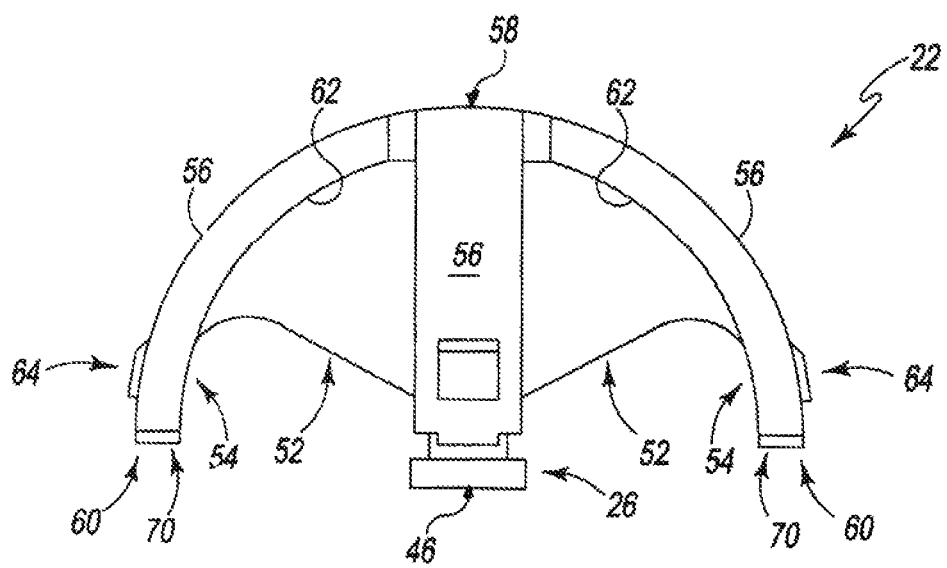
FIG. 7 is a side elevation view of the driver component of FIG. 6.

As shown in FIGS. 6-7, each rib 50 of the driver 22 includes a reinforcing strut 52 and an arm 54. The struts 52 may be arranged to receive the rotary power tool 12 to transmit rotational power from the power tool 12 to the hemispherical component 18. In one example, when the shank 26 of the driver 22 engages the output shaft 28 of the rotary power tool 12 and the driver 22 is coupled to the hemispherical component 18, the output shaft 28 may at least partially engage the reinforcing struts 52 so that rotational power from the output shaft 28 is transmitted to the hemispherical component 18 through the struts 52. In this way, the reinforcing struts 52 may provide an engagement interface between the rotary power tool 12 and the driver 22, in addition to the engagement interface provided by the shank 26. It should be appreciated, however, that the struts 52 may be spaced apart from the output shaft 28 when the shank 26 is coupled to the output shaft 28 (i.e., the struts 52 do not provide the engagement interface).

Each arm 54 of the driver 22 has a curved outer surface 56 that extends from an apex 58 of the driver 22 to an arm tip 60. Each surface 56 is configured to engage the concave inner surface 30 of the hemispherical component 18. As shown in FIG. 7, each arm 54 has a curved inner surface 62 that is positioned opposite from the outer surface 56. Each strut 52 extends between the core 44 and one of the inner surfaces 62 of the arms 54.

As described above, the assembly 10 includes a plurality of locking features 24 configured to secure the driver 22 to the hemispherical component 18 and thereby axially fix those components together for rotation by the tool 12. In the illustrative embodiment, the locking features 24 include a plurality of tabs 64, which are formed on the driver 22. Specifically, as shown in FIG. 7, each tab 64 extends outwardly from the curved outer surface 56 of an arm 54. The tabs 64 are illustratively shown substantially rectangular-shaped. It should be appreciated that in other embodiments the tabs 64 may take the form of other suitable geometric shapes.

Returning now to FIG. 2, each tab 64 of the driver 22 is sized to be received in a corresponding aperture 66 defined in the hemispherical component 18. Each aperture 66 is positioned adjacent to the rim surface 34 and extends through the surfaces 30, 32 of the component 18. In other embodiments, the apertures 66 may not extend through the surface 32 and may be formed as, for example, closed slots defined in the inner surface 30.

In the illustrative embodiment, the locking features 24 of the assembly 10 also include a plurality of shoulders 70 that extend outwardly from the tips 60 of the arms 54 of the driver 22. The shoulders 70 are illustratively shown with a substantially rectangular shape, but it should be appreciated that the shoulders 70 may take the form of other suitable geometric shapes. As shown in FIGS. 1 and 2, each shoulder 70 is sized to be positioned between a pair of retainers 72 that extend from the rim surface 34 of the hemispherical component 18. The shoulders 70 and the retainers 72 provide additional axial fixation between the component 18 and the driver 22.

It should be appreciated that in other embodiments some combination of the shoulders 70, tabs 64, retainers 72, and apertures 66 may be omitted. It should also be appreciated that in other embodiments the assembly 10 may include additional or alternative locking features. Such locking features may include fasteners such as screws, pin and slot arrangements, and so forth.

As shown in FIG. 2, each of the cutting teeth 20 includes a pair of sidewalls 74, 76, which extend outwardly from the outer surface 32. An outer wall 78 extends between and connects the sidewalls 74, 76. Each cutting tooth 20 has an elongated cutting edge 80 that is formed by the walls 74, 76, 78. The walls 74, 76, 78 further cooperate to define the passageway 40 that opens into the oblong slot 38 positioned below each tooth 20. During the hip arthroplasty procedure, the cutting edge 80 of each tooth 20 is configured to engage the concave surface of a patient's acetabulum to ream or resect the bone, and resected bone is advanced along the corresponding passageway 40, through the slot 38, and into the cavity 42 of the hemispherical component 18.

Figure 3:
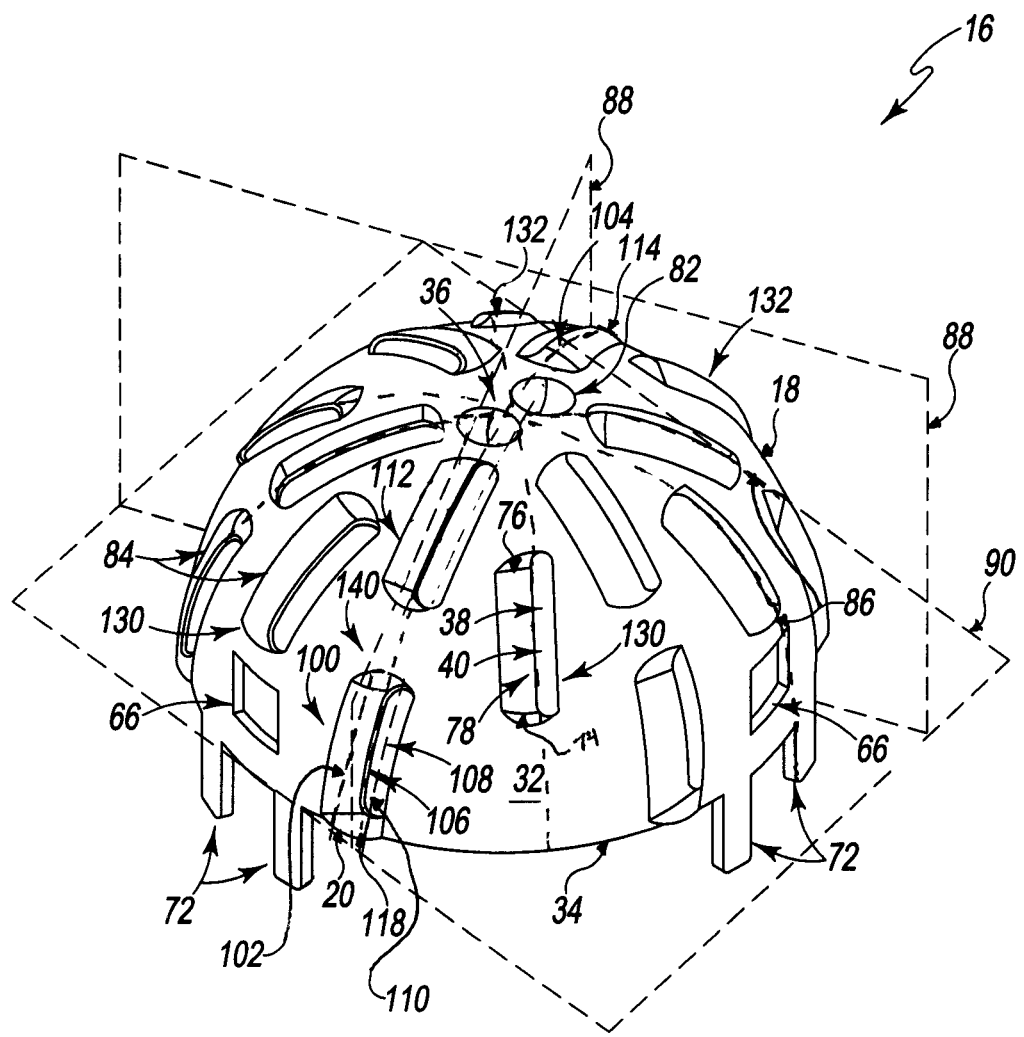
FIG. 3 is a perspective view of a cutting head component of the acetabular surgical instrument assembly of FIG. 1.
Figure 4:
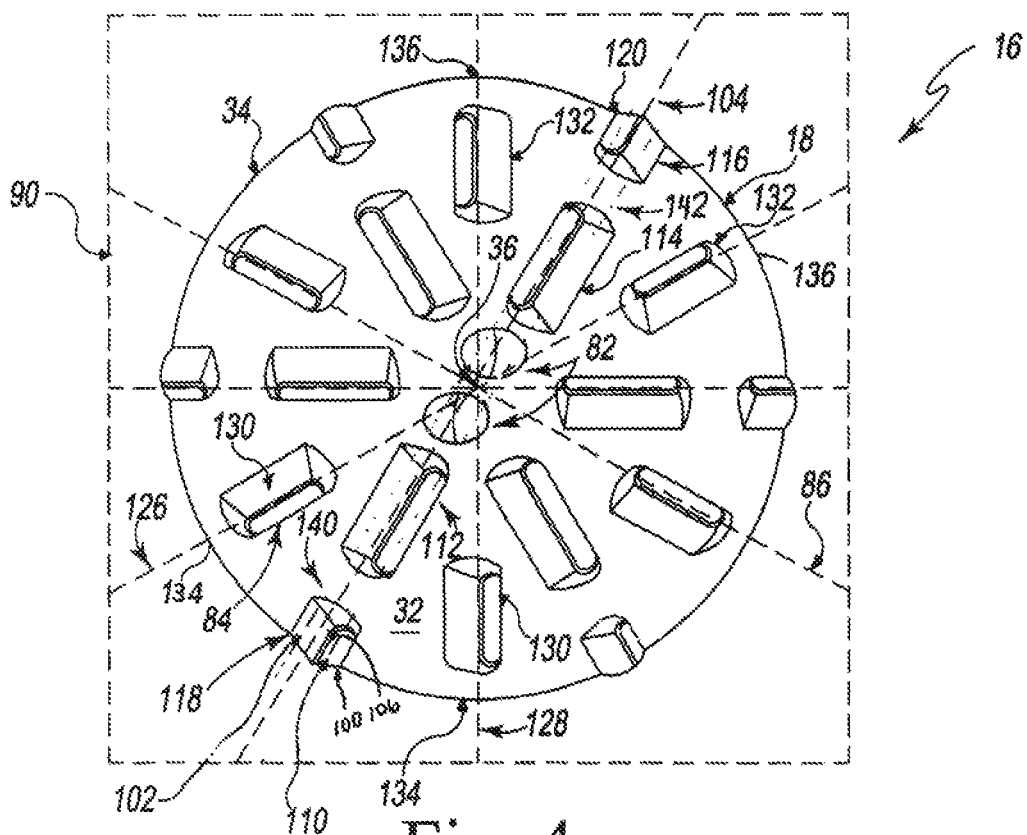
FIG. 4 is a plan view of the cutting head component of FIG. 3.
Figure 5:
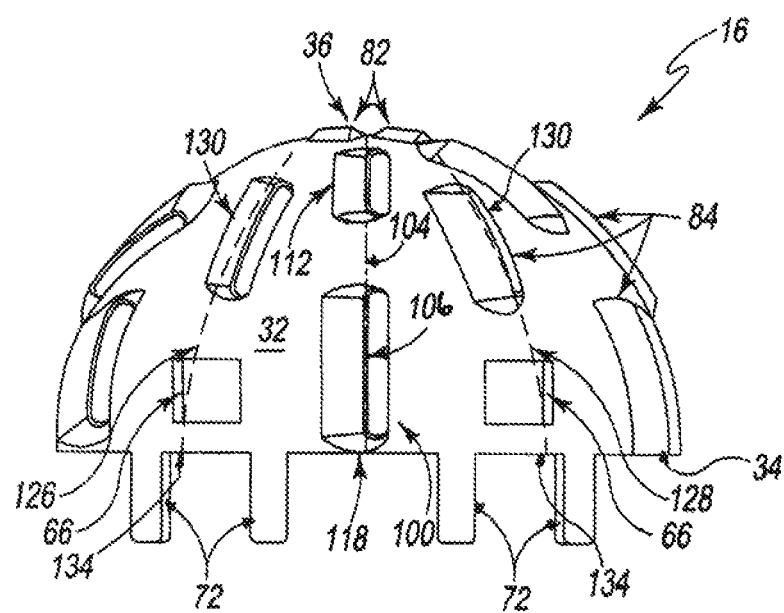
FIG. 5 is a side elevation view of the cutting head component of FIG. 3.

Referring now to FIGS. 3-5, the cutting teeth 20 are shown arranged on the convex outer surface 32 of the hemispherical component 18. As described in greater detail below, the cutting teeth 20 are oriented and positioned on the surface 32 to provide a uniform cutting pattern in the patient's acetabulum. As shown in FIG. 3, the cutting teeth 20 include a number of cutting teeth 82 that are positioned near the apex 36 of the component 18 and a number of elongated cutting teeth 84 positioned between the rim 34 and the apex 36 on one of a number of imaginary arced lines 86.

In the illustrative embodiment, each arced line 86 has a radius (not shown) that is equal to the radius of the convex outer surface 32. Each arced line 86 is also positioned in a corresponding imaginary plane 88 extending through the apex 36 of the component 18. As shown in FIG. 3, each imaginary plane 88 extends orthogonal to an imaginary plane 90 defined by the rim 34 of the component 18.

The elongated cutting teeth 84 share a number of features, which are described in greater detail in regard to elongated cutting tooth 100. For example, as shown in FIGS. 3-5, the elongated cutting tooth 100 has a longitudinal axis 102 that extends parallel to an arced line 104. The cutting tooth 100 has a cutting edge 106 that is positioned on the same arced line 104. An oblong cutting slot 108 positioned below the cutting tooth 100 also has a longitudinal axis 110 that extends parallel to the arced line 104. Those features are shared by the other elongated cutting teeth 84.

In addition to the cutting tooth 100, cutting teeth 112, 114, and 116 are also positioned on the arced line 104. The cutting teeth 100, 112 are positioned on the arced line 104 between the apex point 36 and a point 118 on the rim 34, while the cutting teeth 114, 116 are positioned on the arced line 104 between the apex point 36 and another point 120 on the rim 34. As a result, the cutting teeth 100, 112 are positioned on one side of the component 18, while the cutting teeth 114, 116 are positioned on the opposite side of the component 18.

As shown in FIGS. 3-4, the spacing and positioning of the elongated cutting teeth 84 vary between consecutive arced lines 86. For example, arced lines 126, 128 are positioned consecutively on each side of the arced line 104, and elongated cutting teeth 130, 132 are positioned on each of the arced lines 126, 128. In the illustrative embodiment, a cutting tooth 130 is positioned on each of the arced lines 126, 128 between the apex point 36 and a point 134 on the rim 34, while a cutting tooth 132 is positioned on each of the arced lines 126, 128 between the apex point 36 and another point 136 on the rim 34. The cutting teeth 130 are positioned on the arced lines 126, 128 in a gap 140 defined between the cutting teeth 100, 112; as a result, the cutting teeth 100, 112, 130 define a continuous cutting region between the apex 36 and the rim 34 on one side of the component 18. Similarly, the cutting teeth 132 are positioned on the arced lines 126, 128 in a gap 142 defined between the cutting teeth 114, 116. As a result, the cutting teeth 114, 116, 132 define a continuous cutting region between the apex 36 and the rim 34 on other side of the component 18. As shown in FIGS. 3-5, this alternating configuration—four teeth on one arced line, two teeth on the next arced line—defines the spacing and positioning of the elongated teeth 84 on the entire outer surface 32.

In other embodiments the component 18 may include additional or fewer teeth on each arced line. For example, instead of four teeth on one arced line, the hemispherical component may include three teeth, with the teeth on the next consecutive arced lines repositioned to provide a continuous cutting region. It should be appreciated that in other embodiments other teeth arrangements may be used. Additionally, in the illustrative embodiment, the imaginary arced lines 86 are spaced apart by approximately 30 degrees. It should be appreciated that in other embodiments, the arced lines 86 may be positioned closer or farther apart.

In other embodiments still, the cutting teeth may be serrated, forward-swept, or formed to include notches. Additionally, in other embodiments, the cutting teeth may have portions that are positioned on one or more spiral or helical lines emanating outward from the apex point 36 toward the rim 34 along the outer surface 32. In that configuration, the teeth may have an oblong shape and be spaced apart from one another on the one or more arced lines.

As described above, the hemispherical component 18 includes a plurality of apertures 66 that are sized to receive tabs 64 of the driver 22. As shown in FIG. 5, each aperture 66 is positioned on one of the arced lines 86 between one of the cutting teeth 84 and the rim 34. In the illustrative embodiment, each aperture 66 is positioned on an arced line 86 with two elongated cutting teeth 84. The apertures 66 are illustratively rectangular-shaped, but it should be appreciated that the apertures 66 may take the form of other suitable geometric shapes. The hemispherical component 18 is illustratively formed to include four apertures 66 spaced approximately ninety degrees from one another. In other embodiments, the hemispherical component 18 may include more or less than four apertures 66 spaced apart from one another around the rim 34 by more or less than ninety degrees.

As described above, the hemispherical component 18 also includes retainers 72 that provide additional axial fixation between the component 18 and the driver 22. Each retainer 72 is illustratively shown in an upright, pre-assembly position in FIG. 5. In the illustrative embodiment, the retainers 72 extend outwardly from the rim 34 and are aligned with the apertures 66. In other embodiments, the hemispherical component 18 may include more or less retainers 72, which may be spaced apart on the rim 34 by more or less than ninety degrees.

Figure 8:
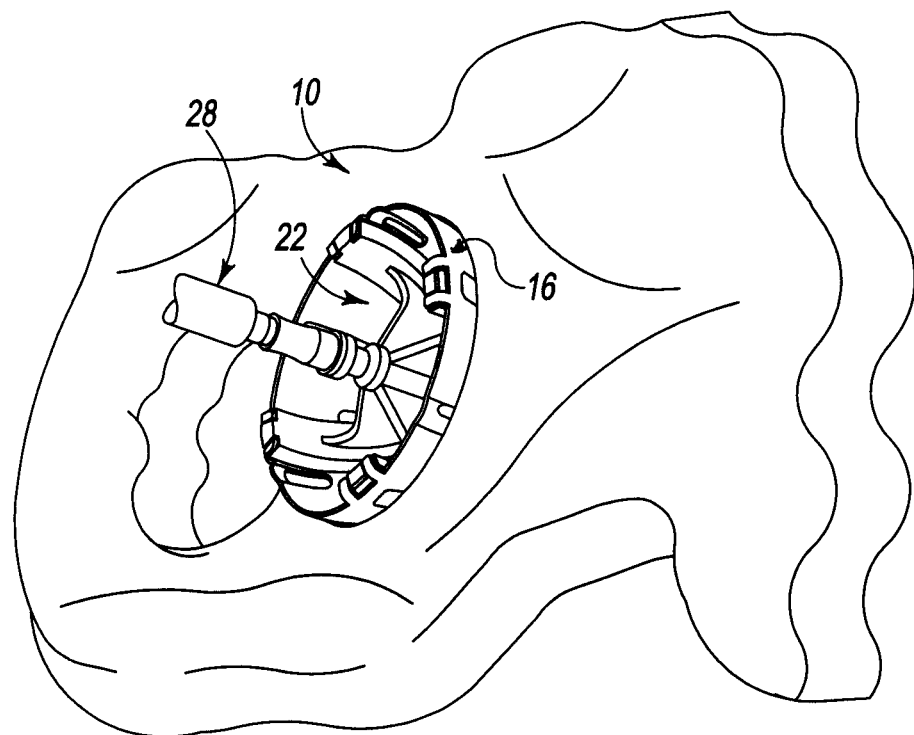
FIG. 8 is a perspective view of the acetabular surgical instrument assembly of FIG. 1 secured to the rotary power tool and engaged with a patient's natural acetabulum.

In use, the reamer 16 and the driver 22 are first aligned along the rotational axis 48 so that the cavity 42 defined by the reamer 16 confronts the apex 58 of the driver 22 as shown in FIG. 2. Then, the driver 22 is advanced toward the reamer 16 along the rotational axis 48 and into the cavity 42 so that the tabs 64 of the driver 22 are received in the apertures 66 of the reamer 16. Once the tabs 64 have been received in the apertures 66, axial movement of the driver 22 relative to the reamer 16 along the axis 48 is substantially prevented, and the driver 22 and the reamer 16 are coupled for common rotation with one another about the axis 48. After the tabs 64 have been received in the apertures 66, the retainers 72 are moved from the upright, pre-assembly position shown in FIG. 5 to the assembled position shown in FIG. 1. At that point, the shoulders 70 are positioned between the retainers 72 as shown in FIG. 1. Once the shoulders 70 are positioned between the retainers 72, the shank 26 is engaged with the output shaft 28 of the power tool 12 as shown in FIG. 1. The reamer 16 is then advanced into contact with bone while rotational power is being generated by the tool 12 to activate the reamer 16 as shown in FIG. 8.

After use, the shank 26 of the driver 22 is first disengaged with the output shaft 28 of the power tool 12. The retainers 72 may be moved to the upright position of FIG. 5 and the driver 22 moved away from the reamer 16 along the axis 48 so that the tabs 64 are positioned outside of the apertures 66. At that point, the driver 22 may be decoupled from the reamer 16. The driver 22 may then be disposed of, and the reamer 16 may be treated in preparation for further use. For example, the reamer 16 may be heat-treated in an autoclave, or other similar processing equipment.

Figure 9:
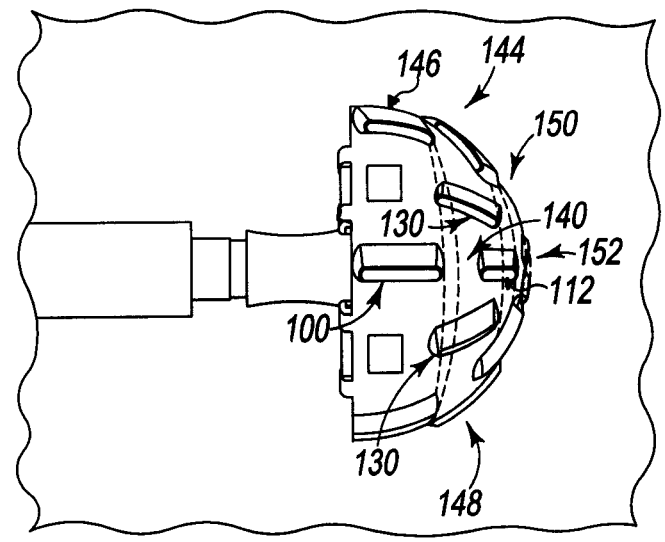
FIG. 9 is a side elevation view of a cutting pattern produced by the acetabular surgical instrument assembly of FIG. 1 when reaming the patient's natural acetabulum.

Referring now to FIG. 9, the orthopaedic surgical instrument assembly 10 is shown in use with the rotary power tool 12 during a hip arthroplasty procedure. Rotational power generated by the power tool 12 is transmitted to the reamer 16 through the driver 22 as discussed above. As the reamer 16 rotates, the cutting teeth 20 ream the patient's natural acetabulum so that the orthopaedic surgical instrument assembly 10 produces a uniform cutting pattern 144, as shown in FIG. 9.

The reamer 16 includes four cutting sections 146, 148, 150, 152 used to produce the pattern 144 as shown in FIG. 9. The cutting sections 146, 148, 150 are defined by the teeth 84, and the cutting section 152 is defined by the teeth 82. The teeth 84 are positioned such that the teeth 84 on consecutive arced lines 86 overlap with one another in each of the cutting sections 146, 148 as shown in FIG. 9. Using the cutting section 146 as an example, the teeth 130 aligned with the gap 140 between the teeth 100, 112 overlap with the tooth 100 in the cutting section 146. As shown in FIG. 9, the cutting section 146 overlaps with the cutting section 148, the cutting section 148 overlaps with the cutting section 150, and the cutting section 150 overlaps with the cutting section 152. In use, each of the cutting sections 146, 148, 150, 152 of the reamer 16 cooperate to uniformly ream the patient's acetabulum to produce the pattern 144.

Figure 10:
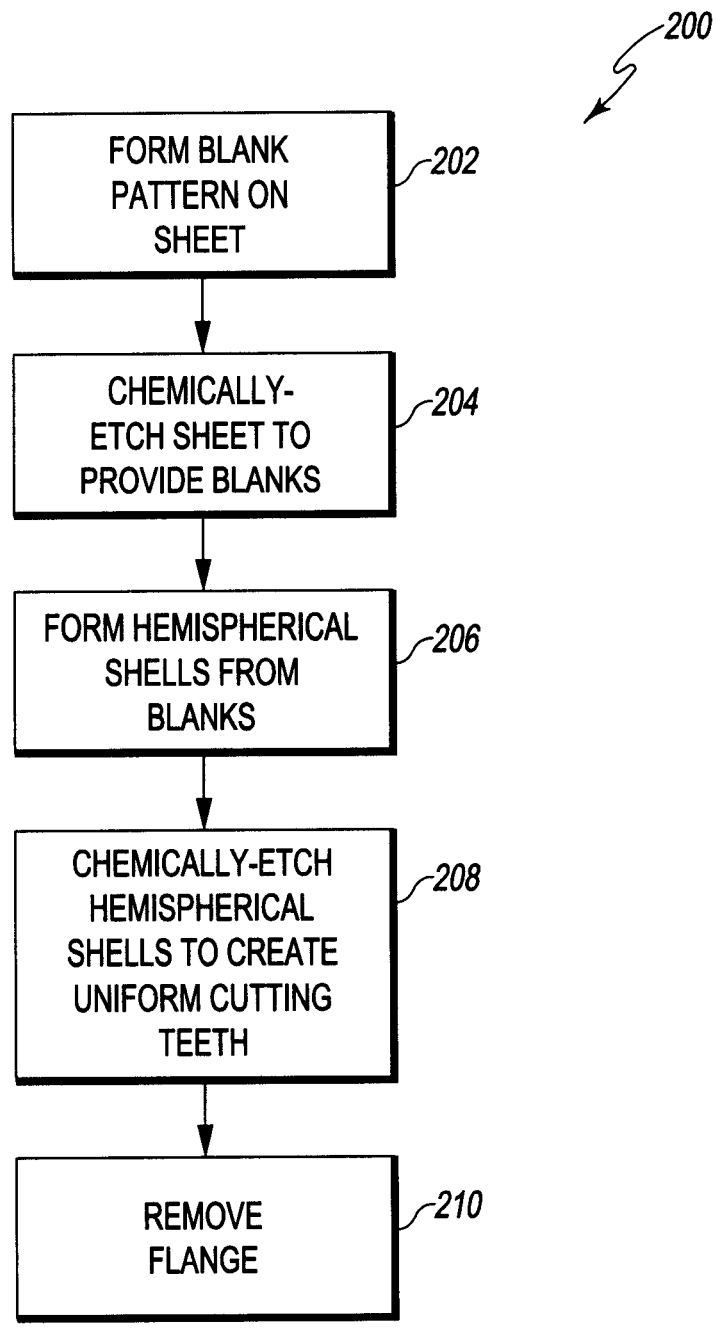
FIG. 10 is a simplified diagram of a method of producing the acetabular surgical instrument assembly of FIG. 1.

Referring now to FIG. 10, a method 200 of manufacturing the hemispherical component 18 is shown. As described in greater detail below, the method includes forming a blank pattern on a metallic sheet, such as the sheet shown in FIG. 11. The metallic sheet may be chemically-etched to obtain one or more metallic blanks, as show in FIG. 12. The metallic blank may be formed into a hemispherical shell (see FIG. 13) via a hydroforming process. The shell is then further chemically-etched to form the hemispherical component 18.

Figure 11:
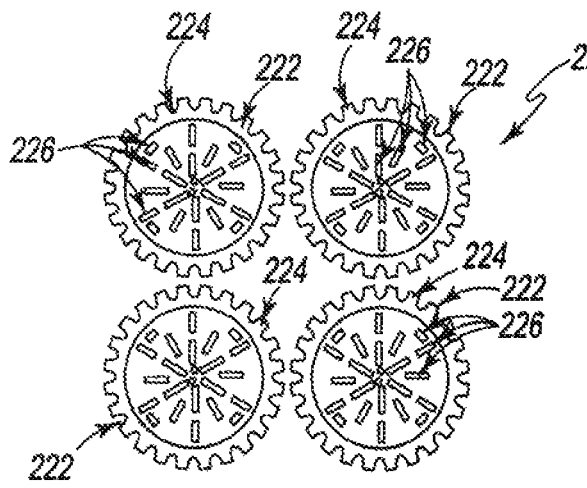
FIG. 11 is a plan view of a sheet of metallic blanks prior to a chemical-etching operation of the method of FIG. 10.

The method 200 begins with block 202 in which a plurality of blank patterns 222 are formed on a sheet 220 as shown in FIG. 11. To do so, the sheet 220 may be first cleaned with a suitable chemical solution to remove debris or contaminants from the sheet 220. A photo-resistant film may then be applied to both sides of the sheet 220. When the film is exposed to a specific set of lights, portions of the film may be removed to expose areas of the metallic sheet. In the illustrative embodiment, the photo-resistant film is exposed to ultraviolet light so that the patterns 222 are formed in the photoresist film. In the illustrative embodiment, each pattern 222 includes an outer rim 224 and a plurality of stenciled shapes 226 arranged on each side of the sheet 220. The configuration of the stenciled shapes 226 is based on the desired locations and arrangement of the cutting teeth 86 and apertures 66 of the hemispherical component 18. In one embodiment, the sheet 220 may include sixteen blank patterns.

The method may advance to block 204 in which the sheet 220 is chemically-etched to form a plurality of blanks 230. To do so, an etchant is applied to the sheet 220 by spraying a chemical etchant onto the sheet 220 to dissolve the metal in the exposed areas mentioned above. For example, the etchant fills the portions of the sheet 220 located between the outer rims 224 of adjacent patterns 222 and dissolves the material in those areas. In the illustrative embodiment, the etchant used with the stainless-steel sheet 220 is ferric chloride. The process may be performed by a number of commercial providers such as, for example, Tecomet of Woburn, Mass., located at 170 New Boston Street, 01801. It should be appreciated that in other embodiments other etchants may be used depending on the material of the sheet. When the etching process is complete, a blank 230 (see FIG. 12) is formed. Following completion of the etching process, each blank 230 may be treated using a suitable chemical solution to remove the photoresist film. For example, a sodium hydroxide-based solution may be used to remove the photoresist film from the blank 230.

Figure 12:
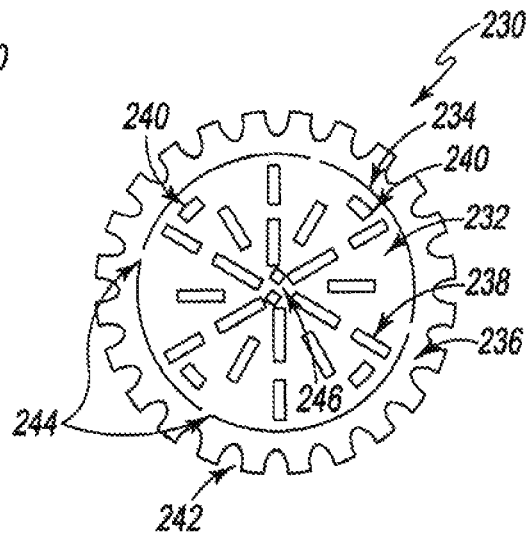
FIG. 12 is a perspective view of one of the metallic blanks of FIG. 11 after the chemical-etching operation of the method of FIG. 10.

As shown in FIG. 12, the blank 230 includes a body 232 circumscribed by a circle 234, and a flange 236. The stenciled shapes 226 are formed in the body 232 of the blank 230. The shapes 226 include a plurality of teeth shapes 238 and a plurality of aperture shapes 240. In addition, a plurality of notches 242 are formed in the flange 236 to give the flange 236 a gear-like appearance. The plurality of teeth shapes 238 and the plurality of aperture shapes 240 are illustratively rectangular-shaped, and the plurality of notches 242 are illustratively U-shaped. As described in more detail below, the notches 242 are provided to reduce wrinkling as a hemispherical shell is formed from the blank 230 in the block 206 of the method 200. Finally, the body 232 of the blank 230 is formed to include discontinuities 244 in the circle 234 that allow the flange 236 to be detached from the body 232.

As described above, the arrangement of the teeth shapes 238 between the circle 234 and a center 246 of the chemically-etched blank 230 is dictated by the desired arrangement of the cutting teeth 20 and the slots 38 between the rim 34 and the apex point 36 of the hemispherical component 18, as best seen in FIGS. 4 and 11. As also described in greater detail below, the apertures 66 of the hemispherical component 18 are formed from the aperture shapes 240 of the chemically-etched blank 230 following the performance of the method 200. The arrangement of the aperture shapes 240 between the circle 234 and the center 246 of the chemically-etched blank 230 is therefore dictated by the desired arrangement of the apertures 66 between the rim 34 and the apex point 36 of the hemispherical component 18, as best seen in FIGS. 4 and 11.

Returning to FIG. 10, the method 200 proceeds to the block 206 in which a hemispherical shell 250 is formed from the chemically-etched blank 230. In the illustrative embodiment, the hemispherical shell 250 is formed by hydroforming the chemically-etched blank 230. In other embodiments, the hemispherical shell 250 may be formed by a stamping operation such as a progressive die stamping operation. In other embodiments, the hemispherical shell 250 may be formed from the chemically-etched blank 230 by a hydraulic forming operation.

The hydroforming process is illustratively a "press" operation in which opposing forces are applied to the chemically-etched blanks 230 to form hemispherical shells. During the hydroforming process, the chemically-etched blanks 230 are positioned in a chamber configured to receive fluid to pressurize the chamber. At the same time that fluid is introduced into the chamber to pressurize the chamber, a punch applies forces to the chemically-etched blanks 230 to raise the metallic material upward within the chamber. The fluid within the chamber applies forces opposing the forces applied by the punch to the chemically-etched blanks 230 to cause the chemically-etched blanks 230 to conform to the shape of the punch as the metallic material is raised upward by the punch within the chamber. The hemispherical shape of the punch matches the desired shape of the chemically-etched blanks 230 following the completion of the hydroforming process, and the punch includes features (i.e., elongated, oblong teeth) that resemble the cutting teeth 20 eventually formed once the method 200 has been completed. The chemically-etched blanks 230 are illustratively hydroformed using the TriForm 610-20-3SC hydroforming machine. The TriForm 610-20-3SC machine may be configured to hydroform a range of different sized chemically-etched blanks 230, and as such, the TriForm 610-20-3SC machine includes the tooling required to hydroform the desired hemispherical shells from the different sizes of chemically-etched blanks 230. For instance, the TriForm 610-20-3SC may include tooling required to hydroform hemispherical shells from chemically-etched blanks 230 having diameters in the range of 36 millimeters to 80 millimeters.

Referring now to FIGS. 15-18, the hydroforming process of the block 206 is shown in which one of the chemically-etched blanks 230 is hydroformed into the hemispherical shell 250. As shown in FIG. 16, the punch contacts the chemically-etched blank 230 to raise the chemically-etched blank 230 upward. A portion 252 of the chemically-etched blank 230 has a somewhat hemispherical shape as shown in FIG. 16. A portion 254 of the chemically-etched blank 230 positioned between the circle 234 and the portion 252 does not have a hemispherical shape, and the notches 242 formed in the flange 236 are shown to be substantially the same size in FIG. 16 as in FIG. 15.

Turning now to FIG. 17, the punch continues to raise the chemically-etched blank 230 upward. The portion 252 of the chemically-etched blank 230 is shown more hemispherical-shaped in FIG. 17 than in FIG. 16, and the portion 254 of the chemically-etched blank 230 has a somewhat hemispherical shape as shown in FIG. 17. The notches 242 are shown shrunken in FIG. 17 compared to FIG. 16. The notches 242 shrink to facilitate the raising of the portions 252, 254 so that those portions have a relatively smooth exterior contour. As such, the notches 242 reduce wrinkling as the chemically-etched blank 230 is hydroformed into the hemispherical shell 250.

Turning now to FIG. 18, the punch continues to raise the chemically-etched blank 230 upward, and the chemically-etched blank 230 is shown raised upward to a greater degree in FIG. 18 than in any of FIGS. 15-17. As such, the portions 252, 254 of the chemically-etched blank 230 are shown more hemispherical-shaped in FIG. 18 than in any of FIGS. 15-17. The notches 242 are shown shrunken in FIG. 18 compared to FIG. 17 such that the notches 242 appear as slivers 242. The desired end of the hydroforming process may be the blank 230 shown in FIG. 18. It should be understood, however, that the chemically-etched blank 230 may be raised to a greater degree by the punch to produce the shell 250 to conclude the hydroforming process.

Figure 13:
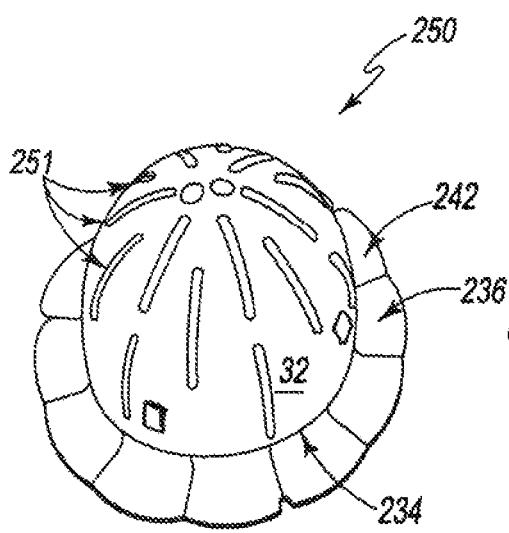
FIG. 13 is a perspective view of a hemispherical shell formed from the metallic blank of FIG. 12 after a press operation of the method of FIG. 10.

Referring now to FIG. 13, the hemispherical shell 250 formed by hydroforming the chemically-etched blank 230 in the block 206 of the process 200 is shown. As a result of the completion of the hydroforming process, the convex outer surface 32 is formed. Raised flanges 251 are formed in the outer surface 32 at the locations of the teeth shapes 238 as shown in FIG. 13, which correspond to the locations of the oblong teeth of the hydroforming punch. As described below, the cutting teeth 20 and the slots 38 are formed in the raised flanges 251 by chemical etching. The aperture shapes 240 are positioned adjacent to the circle 234. As described below, the apertures 66 are formed in or adjacent to the aperture shapes 240. The flange 236 is coupled to the outer surface 32 and includes the slivers 242 as discussed above and shown in FIG. 13.

Returning again to FIG. 10, following completion of the block 206, the method 200 proceeds to the block 208 in which the hemispherical shells 250 are chemically-etched. The block 208 may include a number of sub-operations substantially similar to the sub-operations performed in the block 204. The block 208 may also include a number of sub-operations not performed in the block 204. For example, the block 208 may include a laser etching sub-operation to mark the hemispherical shells 250 with product identification information, a passivation sub-operation to make the hemispherical shells 250 resistant to environmental degradation, and an inspection sub-operation to inspect certain attributes of the hemispherical shells 250 for quality control purposes. It should be understood that the block 208 may include other suitable sub-operations, or that the block 208 may be completed without performing any number of the aforementioned sub-operations.

Figure 14:
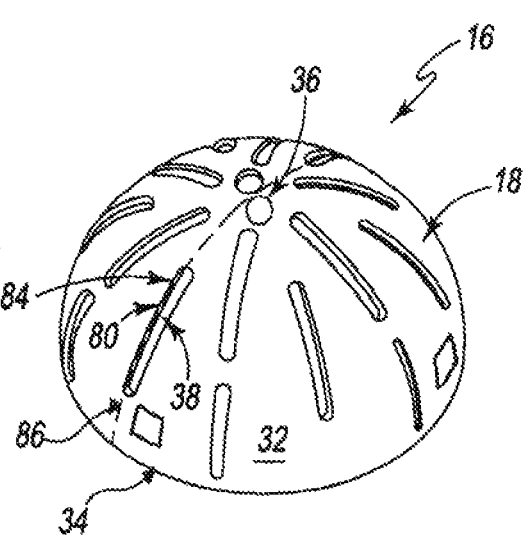
FIG. 14 is a perspective view of the cutting head component of the acetabular surgical instrument assembly produced according to the method of FIG. 10.

Referring now to FIG. 14, the hemispherical shell 250 has been chemically-etched in the block 208 to form the reamer 16. Specifically, the hemispherical shell 250 has been chemically-etched in the block 208 to create the uniform cutting teeth 20 including the cutting edges 80, the slots 38 positioned beneath the cutting edges 80, and the apertures 66. The teeth 20 and the slots 38 are formed in the raised flanges 251, and the apertures 66 are formed in or adjacent to the aperture shapes 240 shown in FIG. 13. The flange 236 has been removed from the outer surface 32 in the block 210. Once the hemispherical shell 250 has been chemically-etched to create the uniform cutting teeth 20, the slots 38, and the apertures 66, and the flange 236 has been removed from the outer surface 32, a hemispherical component 18 of the reamer 16 is produced. The component 18 may be assembled with a reamer driver 22 as described above to form a reamer 16 for use in an orthopaedic surgical procedure.

Figure 19:
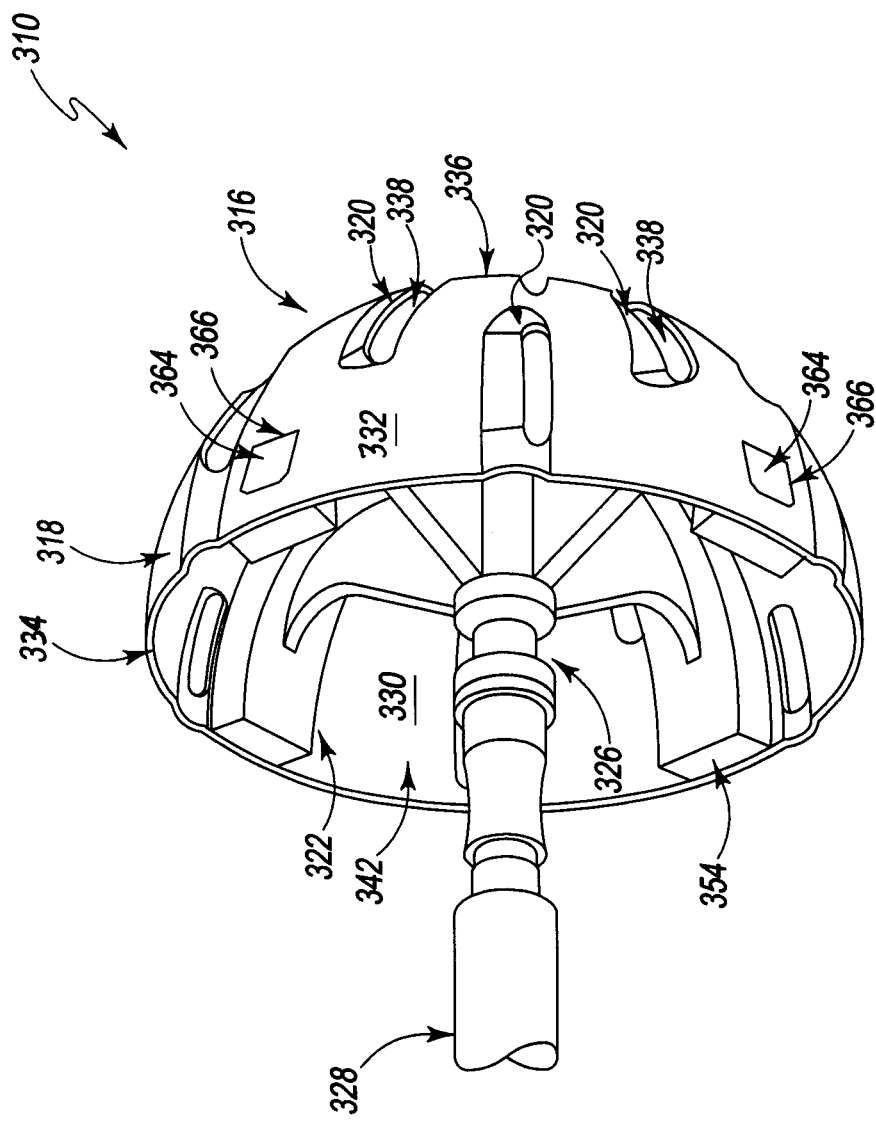
FIG. 19 is a perspective view of another embodiment of an acetabular surgical instrument assembly.

Referring now to FIG. 19, another embodiment of an orthopaedic surgical instrument assembly 310 is illustrated. The orthopaedic surgical instrument assembly 310 is substantially similar to the orthopaedic surgical instrument assembly 10 shown in FIGS. 1-9 and described herein. As such, similar reference numbers in the 300 series indicate features that are common between the orthopaedic surgical instrument assembly 10 and the orthopaedic surgical instrument assembly 310. The description of the orthopaedic surgical instrument assembly 10 is hereby incorporated by reference to apply to the orthopaedic surgical instrument assembly 310, except in instances when it conflicts with the specific description of the orthopaedic surgical instrument assembly 310 with reference to FIG. 19.

The assembly 310 does not include all of the locking features 24 present in the assembly 10. Specifically, as shown in FIG. 19, the assembly 310 does not include retainers (i.e., like the retainers 72) appended to the rim 334 of the reamer 316 and shoulders (i.e., like the shoulders 70) extending outwardly from the arms 354 of the driver 322. Unlike the reamer 16 and the driver 22, the reamer 316 and the driver 322 are coupled to one another only by the use of the tabs 364 of the driver 322 and the apertures 366 of the reamer 316. Accordingly, in use of the assembly 310, the same procedure described above with respect to the assembly 10 is performed to assemble the assembly 310, except for moving the retainers 72 to engage the arms 54 of the driver 22. After use of the assembly 310, the same procedure described above with respect to the assembly 10 is performed to disassemble the assembly 310, except for moving the retainers 72 to the upright, pre-assembly position.

Figure 21:
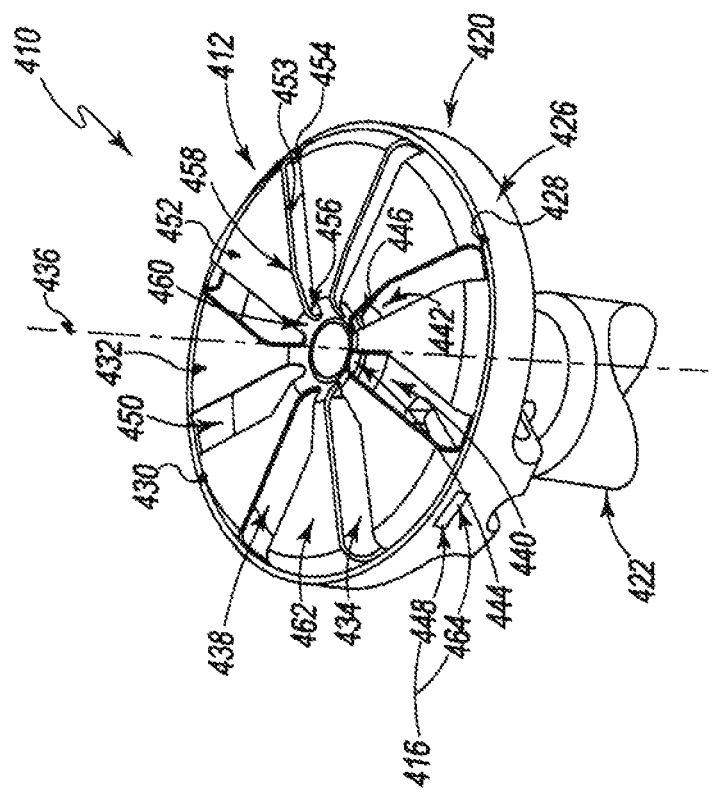
FIG. 21 is another perspective view of the surgical instrument assembly of FIG. 20.
Figure 20:
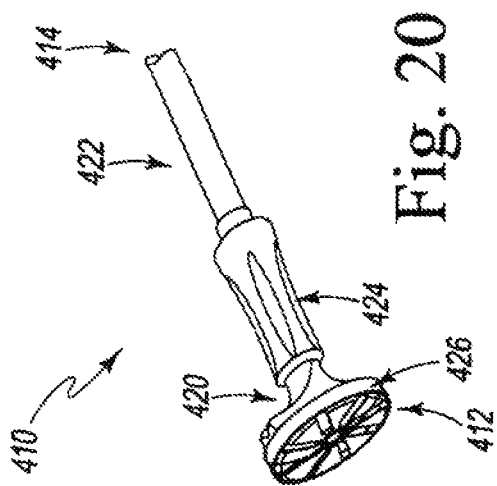
FIG. 20 is a perspective view of yet another embodiment of a surgical instrument assembly.

Referring now to FIGS. 20-21, yet another embodiment of an orthopaedic surgical instrument assembly 410 is shown. The orthopaedic surgical instrument assembly 410 is illustratively a calcar planer reamer assembly configured to resect bone in a surgical procedure such as, for example, a proximal femoral replacement procedure. Similar to the assemblies 10, 310, the orthopaedic surgical instrument assembly 410 is configured for use with a rotary power tool (not shown). The orthopaedic surgical instrument assembly illustratively 410 includes a cutting component 412 and a driver 414. The cutting component 412 is secured to the driver 414 via a plurality of locking features 416 that, as described in greater detail below, permit the cutting component 412 to be fixed to the driver 414 during the surgical procedure and detached from the driver 414 following the surgical procedure.

Referring now to FIG. 20, the driver 414 includes a shank (not shown) configured to be removably coupled to the rotary power tool. When the rotary power tool is attached, rotary power generated by the rotary power tool is transmitted to the cutting component 412 via the driver 414. In that way, the driver 414 acts as the driver component for the assembly 410.

The driver 414 is illustratively formed as a polymeric component, but it should be appreciated that in other embodiments the driver 414 may be formed as a composite material. The driver 414 may be formed, for example, from injection-molded plastic. In other embodiments, part of the driver 414 may be formed from plastic while other parts of the driver 414 may be formed from metal. In still other embodiments, the driver 414 may be exclusively formed from a metallic material.

In addition to the shank, the driver 414 includes a head 420 and a shaft 422 extending between the head 420 and the shank as shown in FIG. 20. The head 420 is configured to couple to the cutting component 412 as described in greater detail below. A sleeve 424 illustratively surrounds the shaft 422 adjacent the head 420 as shown in FIG. 20.

The driver 414 includes a head 420 configured to couple to the cutting component 412. The head 420 of the driver 414 includes an outer wall 426, an inner wall 428, and a circular rim 430 extending between the outer wall 426 and the inner wall 428. The outer wall 426 and the inner wall 428 are illustratively circular-shaped as shown in FIG. 21. The inner wall 428 extends inwardly from the circular rim 430 to define a cavity 432 in the driver 414. A hub 434 of the driver 414 is positioned in the cavity 432 as best seen in FIG. 21 and described in more detail below.

Referring now to FIG. 21, the hub 434 of the head 420 is configured to rotate about a central axis 436 of the driver 414. The hub 434 includes a disc 438 and a pedestal 440 extending outwardly from the center of the disc 438 along the axis 436. The pedestal 440 includes a circular body 442 and a circular neck 444 coupled to and extending outwardly from the body 442. The body 442 has a greater diameter than the neck 444 such that a shoulder 446 is provided by the pedestal 440 as shown in FIG. 21. As described in greater detail below, the cutting component 412 engages the shoulder 446 when the cutting component 412 is coupled to the driver 414.

In the illustrative embodiment, the locking features 416 include a plurality of apertures 448, which are formed on the head 420 of the driver 414. As shown in FIG. 21, each aperture 448 is positioned adjacent the rim 430 and extends through the walls 426, 428 of the head 420. In other embodiments, the apertures 448 may not extend through the outer wall 426 and may be formed as, for example, closed slots defined in the inner wall 428. The apertures 448 are illustratively shown as rectangular-shaped, but it should be appreciated that the apertures 448 may take the form of other geometric shapes.

The cutting component 412 of the assembly 410 is illustratively formed as a metallic component. In the illustrative embodiment, the cutting component 412 is formed, for example, from titanium or stainless steel. In other embodiments, part of the cutting component 412 may be formed from a polymeric material such as, for example, plastic, while the resecting surfaces are coated with a metallic material. For example, a base 450 of the cutting component 412 may be formed from a polymeric material, while cutting teeth 452 of the cutting component 412 may be coated or formed with a metallic cutting edge.

As indicated above, the cutting component 412 includes the base 450 and the cutting teeth 452. The cutting teeth 452 are interconnected with and extend outwardly from the base 450 as shown in FIG. 21. The cutting teeth 452 include a plurality of cutting edges 453 configured to resect bone when the assembly 410 is used in the surgical procedure. Each of the teeth 452 includes generally curved sidewalls 454, 456 and a generally planar outer wall 458 connecting the sidewalls 454, 456. As shown in FIG. 21, each sidewall 454 extends outwardly away from the base 450, and each sidewall 456 extends inwardly toward the base 450 to a ring 460. The outer walls 458 of the teeth 452 cooperate to define generally planar resection surfaces 462 of the cutting component 412.

The cutting component 412 includes the ring 460 interconnected with the sidewalls 456 of the cutting teeth 452 as shown in FIG. 21. The ring 460 is sized to engage the shoulder 446 of the driver 414 to resist relative movement between the driver 414 and the cutting component 412 along the axis 436 when the component 412 is coupled to the driver 414.

In the illustrative embodiment, the locking features 416 include a plurality of tabs 464, which are formed on the base 450 of the cutting component 412. The tabs 464 extend outwardly from the base 450. When the cutting component 412 is coupled to the driver 414 as shown in FIG. 21, the plurality of tabs 464 are received in the plurality of apertures 448 and the ring 460 engages the shoulder 446 as indicated above. In addition, the base 450 is received in the cavity 432 and the teeth 452 extend outwardly from the cavity 432 to define the resection surfaces 462.

In use, the cutting component 412 and the driver 414 are first aligned along the rotational axis 436 so that the cavity 432 defined by the driver 414 confronts the base 450 of the cutting component 412 as shown in FIG. 21. Then, the cutting component 412 is advanced toward the driver 414 along the rotational axis 436 and into the cavity 432 so that the tabs 464 of the cutting component 412 are received in the apertures 448 of the driver 414 and the ring 460 of the cutting component 412 engages the shoulder 446 of the driver 414. Once the tabs 464 have been received in the apertures 448 and the ring 460 engages the shoulder 446, axial movement of the cutting component 412 relative to the driver 414 along the axis 436 should be substantially prevented, and the cutting component 412 and the driver 414 should be substantially coupled for common rotation about the axis 436. At that point, the shank of the driver 214 is engaged with an output shaft of the rotary power tool. When rotational power is being generated by the rotary power tool, the resection surfaces 462 of the cutting component 412 are then engaged with bone to resect bone during the surgical procedure.

After use, the shank of the driver 414 is first disengaged with the output shaft of the power tool. The cutting component 412 is moved away from the driver 414 along the axis 436 so that the tabs 464 are positioned outside of the apertures 448. At that point, the cutting component 412 is decoupled from the driver 414. The driver 414 may then be disposed of, and the cutting component 412 may be treated in preparation for further use. For example, the cutting component 412 may be heat-treated in an autoclave, or similar processing equipment.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of manufacturing an orthopaedic surgical instrument, the method comprising:
   applying a first chemical etch to a sheet to form a plurality of blanks including a plurality of stenciled shapes,
   forming a hemispherical shell from a blank of the plurality of blanks, the hemispherical shell including a convex outer surface and a plurality of raised flanges extending outwardly from the convex outer surface, each raised flange of the plurality of raised flanges including at least one of the plurality of stenciled shapes, and
   applying a second chemical etch to hemispherical shell to form a cutting tooth and a cutting edge in each raised flange of the plurality of raised flanges.

2. The method of claim 1, wherein each blank of the plurality of blanks comprises (i) a circular body and (ii) a notched flange coupled to the circular body and having a plurality of notches formed therein, wherein each notch of the plurality of notches has a width, and
   wherein forming the hemispherical shell comprises reducing the width of each notch of the plurality of notches such that the notched flange extends radially from the hemispherical shell.

3. The method of claim 1, wherein forming the hemispherical shell from the blank comprises hydroforming the hemispherical shell from the blank.

4. The method of claim 1, wherein applying the second chemical etch to the hemispherical shell comprises forming a plurality of slots beneath the cutting edges of the cutting teeth.

5. The method of claim 1, further comprising applying a photoresist film to the sheet.

6. A method of manufacturing an orthopaedic surgical instrument, the method comprising:

chemically-etching a sheet to form a plurality of blanks including a plurality of stenciled shapes, wherein each blank of the plurality of blanks comprises (i) a circular body and (ii) a notched flange coupled to the circular body and having a plurality of notches formed therein, forming a hemispherical shell from a blank of the plurality of blanks, the hemispherical shell including a convex outer surface and a plurality of raised flanges extending outwardly from the convex outer surface, each raised flange of the plurality of raised flanges including at least one of the plurality of stenciled shapes, applying a chemical etch to the stenciled shapes to form a cutting tooth and a cutting edge in each raised flange of the plurality of raised flanges, and removing the notched flange from the circular body.

7. The method of claim 6, wherein forming the hemispherical shell from the blank comprises hydroforming the hemispherical shell from the blank.

8. The method of claim 6, wherein chemically-etching the hemispherical shell comprises forming a plurality of slots beneath the cutting edges of the cutting teeth.

9. The method of claim 6, further comprising applying a photoresist film to the sheet.

* * * * *